(12) United States Patent
Holko et al.

(10) Patent No.: US 8,246,620 B2
(45) Date of Patent: Aug. 21, 2012

(54) ADVANCED BURR, APPLIQUE FOR A BURR AND METHOD OF FABRICATING

(76) Inventors: Kenneth Holko, San Diego, CA (US); Thomas D. Peterson, La Mesa, CA (US)

( * ) Notice: Subject to any disclaimer, the term of this patent is extended or adjusted under 35 U.S.C. 154(b) by 373 days.

(21) Appl. No.: 12/314,790

(22) Filed: Dec. 17, 2008

(65) Prior Publication Data

US 2010/0152738 A1      Jun. 17, 2010

(51) Int. Cl.
    *A61B 17/56* (2006.01)
(52) U.S. Cl. .................... 606/76; 606/171; 606/180
(58) Field of Classification Search .......... 606/76, 606/79, 167, 159, 170, 171, 180, 80–85; 451/29.1–29.15; 407/29.1–29.15; 132/75.6, 132/76.4
See application file for complete search history.

(56) References Cited

U.S. PATENT DOCUMENTS

| | | | |
|---|---|---|---|
| 6,190,246 B1 * | 2/2001 | Parrott et al. | 451/540 |
| 6,957,934 B2 * | 10/2005 | Masterson et al. | 407/29.15 |
| 2002/0107521 A1 * | 8/2002 | Petersen et al. | 606/85 |

* cited by examiner

*Primary Examiner* — Cris L Rodriguez
*Assistant Examiner* — Eric Rosen
(74) *Attorney, Agent, or Firm* — H. Jay Spiegel

(57) ABSTRACT

An abrading device including an advanced burr and appliqué for a burr and a new process for making cutting tools for fine material removal applications such as in bone and tissue surgeries. An appliqué sheet is first engineered by CAD with an abrading surface having cutting facets. The appliqué is attached to a surface of a tool blank and then metallurgically bonded and coated by the BRAZOL® or Co—P process. The tool blank has a proximal shank attachable to a driver and a distal surface to which the appliqué is affixed. Since each facet is attached to surrounding facets and then strongly bonded to the tool, the facets do not dislodge when used to abrade a surface of an object. The BRAZOL® or Co—P coating imparts excellent wear resistance and lubricity to the cutting facets. This results in excellent operational and material removal characteristics. This approach to making surgical and fine industrial tools offers engineered flexibility in design rather than process dependent designs.

28 Claims, 9 Drawing Sheets

ADVANCED BURR, APPLIQUE FOR A BURR AND METHOD OF FABRICATING

BACKGROUND OF THE INVENTION

The present invention relates to an advanced burr, appliqué for a burr and method of fabricating. Burr and abrading tools are well known in the medical and manufacturing industries. These tools are used to remove various materials, usually in finish or "fine" work where careful control of amount of material removed is important. Also, these tools must not damage surrounding tissue or machined surfaces either by impact with the surface or by leaving behind particles removed from the tool during abrading operations. Particles released from the tool at high speed also present a safety hazard to the operator.

One well known manufacturing technique is to machine flutes or cutting surfaces in a burr or abrader surface. When operated in a rotational or oscillatory mode, these flutes dig into the object surface and scrape material off. Two problems with this technique are (1) a "kickback" effect when the flutes first make contact, and (2) limitation in flute size, shape and geometry as dictated by the machining process used to create the cutting surface on the burr. This kickback effect can damage surrounding tissue and other material, while size and shape limitations direct usage toward more coarse removal applications. Burr operational speed has been increased to minimize kickback, but this makes the burr more dangerous to use.

Another well known manufacturing technique is to attach hard particles to the tool surface, like diamonds and carbides, by electroplating and/or brazing. While this technique can minimize kickback effect by incorporating particle "randomness," particle release has been and is a problem. In electroplating diamonds, for example, attachment is mechanical rather than metallurgical. Particle release from impact is random since it depends on how much of the diamond particles are covered by the plating. Also, diamonds are subject to fracture on impact, depending on crystal orientation, as demonstrated by the diamond cutting process. Carbides are also subject to fracture. When these tools wear, it is by loss of particles from fracture and release, rather than dulling from deformation. Particularly in surgical applications, even small amounts of these foreign particles that are not recovered can be detrimental to patient health by causing inflammation and sometimes resulting in failure of surgical results, such as when the procedure involves joint replacement failure due to "osteolysis." Osteolysis is a medical term denoting inflammation due to presence of foreign particles. Approximately 20% of total joints eventually fail due to onset of osteolysis.

Applicants have sought to solve the problems of the prior art by developing a process for creating and applying a unique cutting surface to a burr or abrader tool. The resulting tools solve the problems described above. The inventive technique utilizes a continuous "appliqué" that has integral cutting facets. The cutting facets are engineered for a particular application rather than using generic particles or a machined surface. The appliqué is formed on the tool surface and then metallurgically bonded and metallurgically coated by the process known by the registered Trademark BRAZOL. This process has been successfully used for over a decade in the surgical industry and is described in U.S. Pat. Nos. 5,022,555; 5,149,597; 5,133,728; 5,135,533; and 5,707,276 all granted to Applicants. Bonding and coating may also be done by the "Cobalt-Phosphorous" technique described in U.S. Pat. Nos. 5,358,547 and 5,649,994 granted to Applicant Holko. These patents are hereby incorporated herein by reference including the disclosures in these patents of numerous formulations of metallurgical bonding materials, each of which is incorporated by reference herein as if specifically set forth herein.

SUMMARY OF THE INVENTION

The present invention relates to an abrading device comprising an advanced burr and appliqué for a burr and a new process for making cutting tools for fine material removal applications such as bone and tissue surgeries. An appliqué sheet is first engineered by CAD with an abrading surface comprising cutting facets designed for the particular application. The appliqué is attached to a surface of a tool blank comprising a burr or abrader tool blank and then metallurgically bonded and coated by the BRAZOL® or Co—P process. The tool blank has a proximal shank attachable to a driver and a distal surface to which the appliqué is affixed. Since each facet is attached to surrounding facets and then strongly bonded to the tool, the facets do not dislodge when used to abrade a surface of an object, as occurs with other tools. The BRAZOL® or Co—P coating imparts excellent wear resistance and lubricity to the cutting facets. This results in excellent operational and material removal characteristics. This approach to making surgical and fine industrial tools offers engineered flexibility in design rather than process dependent designs.

As described in U.S. Pat. Nos. 5,135,533 and 5,149,597, the BRAZOL® coating may be described as follows:

(1) The first constituent material which is used in the coating consists of a brazing alloy in a fine powder form, the alloy being made up of, by weight, 14% Chromium, 0.1% Silicon, 0.2% Iron, 10% Phosphorus and the balance Nickel. One example of such an alloy is known by the Trademark NICROBRAZ 50, a Trademark of the Wall Colmonoy Corporation.

(2) The inventive coating material is prepared by mixing the above described brazing alloy with a further brazing alloy in fine powder form which is made up of, by weight, 3.5% Silicon, 1.9% Boron, 1.5% Iron and the balance Nickel. Examples of this further brazing alloy are known by the Trademarks NICROBRAZ 135 owned by the Wall Colmonoy Corporation and AMDRY 790 owned by Alloy Metals, Inc.

(3) For optimal results, the two above-mentioned brazing alloy powders are mixed together in the ratio of 80% of the first mentioned brazing alloy powder and 20% of the second mentioned brazing alloy powder. For optimal results, the powdery nature of the alloys should be to a particle size of −200 mesh or finer. The Co—P process is described hereinafter.

(4) As disclosed in the patent, for example, in the method of coating a metallic surgical saw blade with the inventive coating, the surface of the saw blade is first carefully cleaned and is then coated with a binder material. Thereafter, the coating material is dusted onto the surface and adheres thereto due to the presence of the binder. Thereafter, the coating is metallurgically bonded to the metallic surface by heating to the melting temperature of the coating material in a series of heating steps, preferably performed in a vacuum furnace. The analogous technique may be used to both metallurgically bond the appliqué to the tool surface and to coat the appliqué.

Accordingly, it is a first object of the present invention to provide an advanced burr, appliqué for a burr and method of fabricating it.

It is a further object of the present invention to provide such a burr in which a burr blank is provided having an outer surface and an appliqué is bonded onto that surface.

It is a further object of the present invention to provide such a burr wherein the appliqué has an outer surface providing a cutting pattern designed to afford the user a custom cutting action for a desired specific application.

It is a still further object of the present invention to provide such an appliqué with a cutting pattern including sharp facet points provided in a desired pattern.

It is a still further object of the present invention to provide such an appliqué with the provision of holes facilitating communication of the bonding material from the interface between the appliqué and the tool blank and the surface of the appliqué.

It is a still further object of the present invention to utilize BRAZOL® coating or the Co—P coating as the bonding material.

These and other objects, aspects and features of the present invention will be better understood from the following detailed description of the preferred embodiments when read in conjunction with the appended drawing figures.

SPECIFIC DESCRIPTION OF THE PREFERRED EMBODIMENTS

The process of the present invention begins by designing a cutting surface pattern by computer aided design (CAD) as seen in FIGS. 2a-4b. The preferred cutting facet layouts are shown in these figures. Also shown are the protrusions or plateaus and cutting edges that will be present on the final appliqué. Three exemplary designs are described but an unlimited number of designs are possible with various cutting facet sizes, shapes, orientations, spacings, and depths.

Figure 2A:
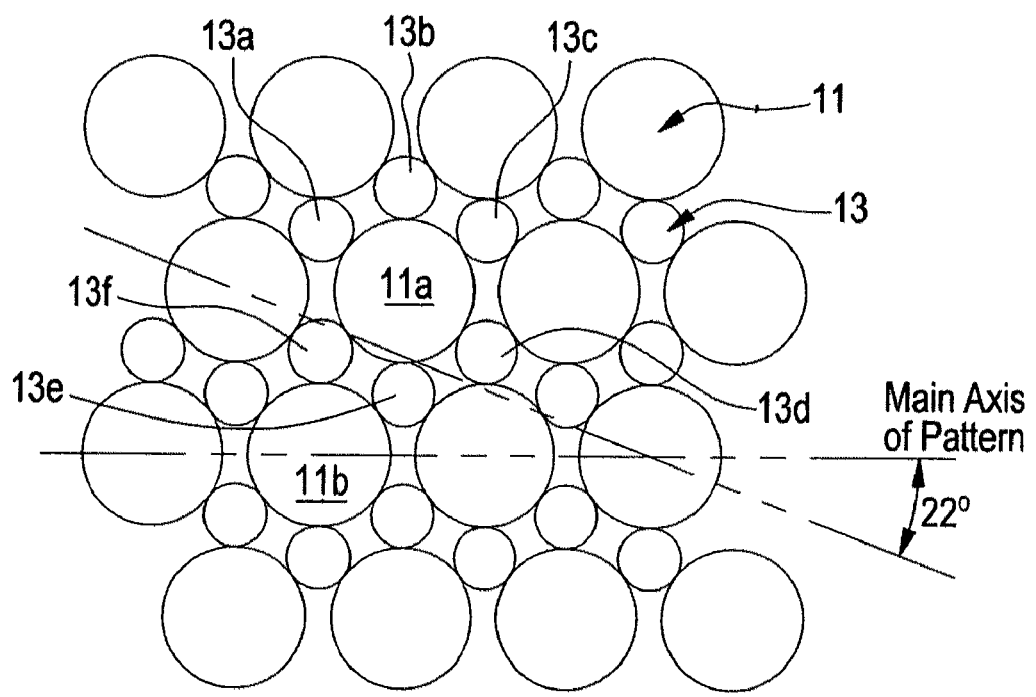
FIGS. 2a and 2b show an appliqué CAD drawing (2a) and resultant burr SEM photomicrograph (2b) for "cylindrical" cutting design.
Figure 2B:
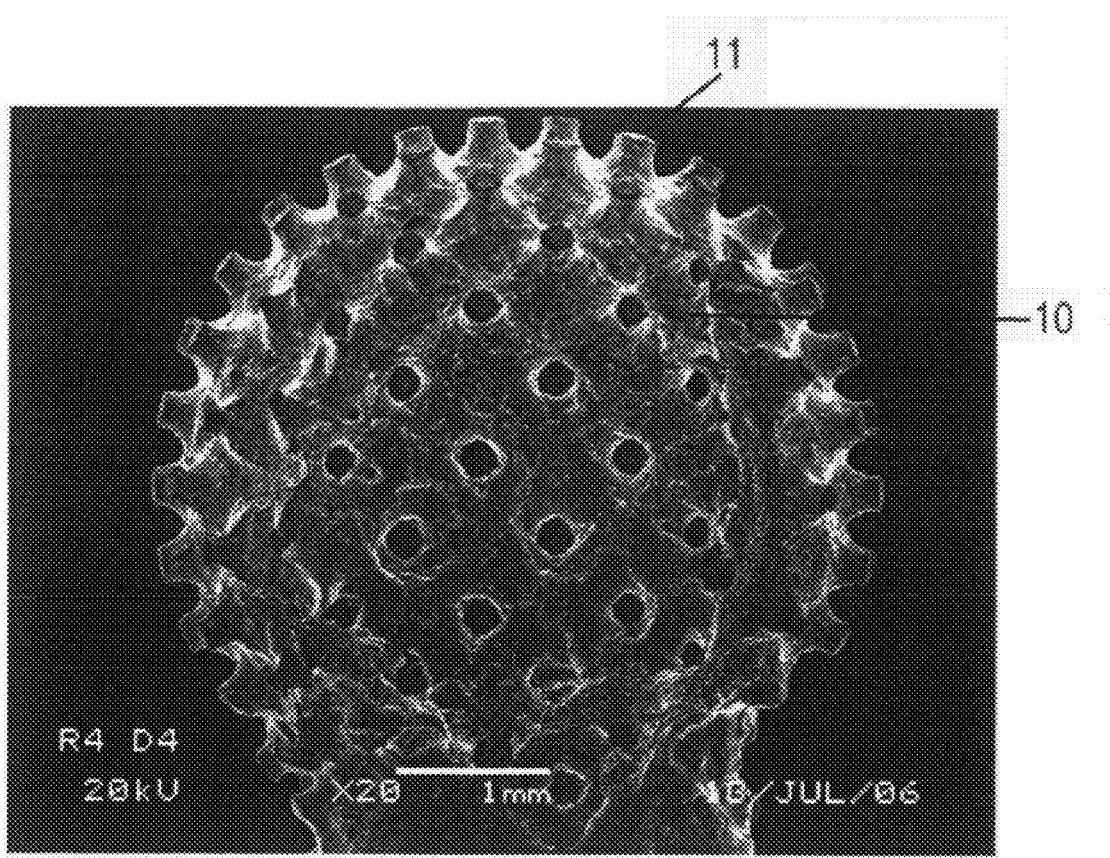

With reference to FIGS. 2a and 2b, a first example of a cutting facet layout in accordance with the teachings of the present invention is shown to include a plurality of protrusions 11 and a plurality of smaller holes 13. As seen in the photomicrograph of FIG. 2b, the protrusions 11 are generally cylindrical at their distal terminations and widen out proximally as they approach the base of the appliqué 10. The smaller holes 13 are located such that, as best seen in FIG. 2a, six holes 13 surround each protrusion 11 with each hole forming this surrounding configuration for a plurality of protrusions 11. Thus, for example, the protrusion 11a is surrounded by the holes 13a, 13b, 13c, 13d, 13e and 13f. For example, the holes 13e and 13f also contribute to surrounding the protrusion 11b.

Figure 3A:
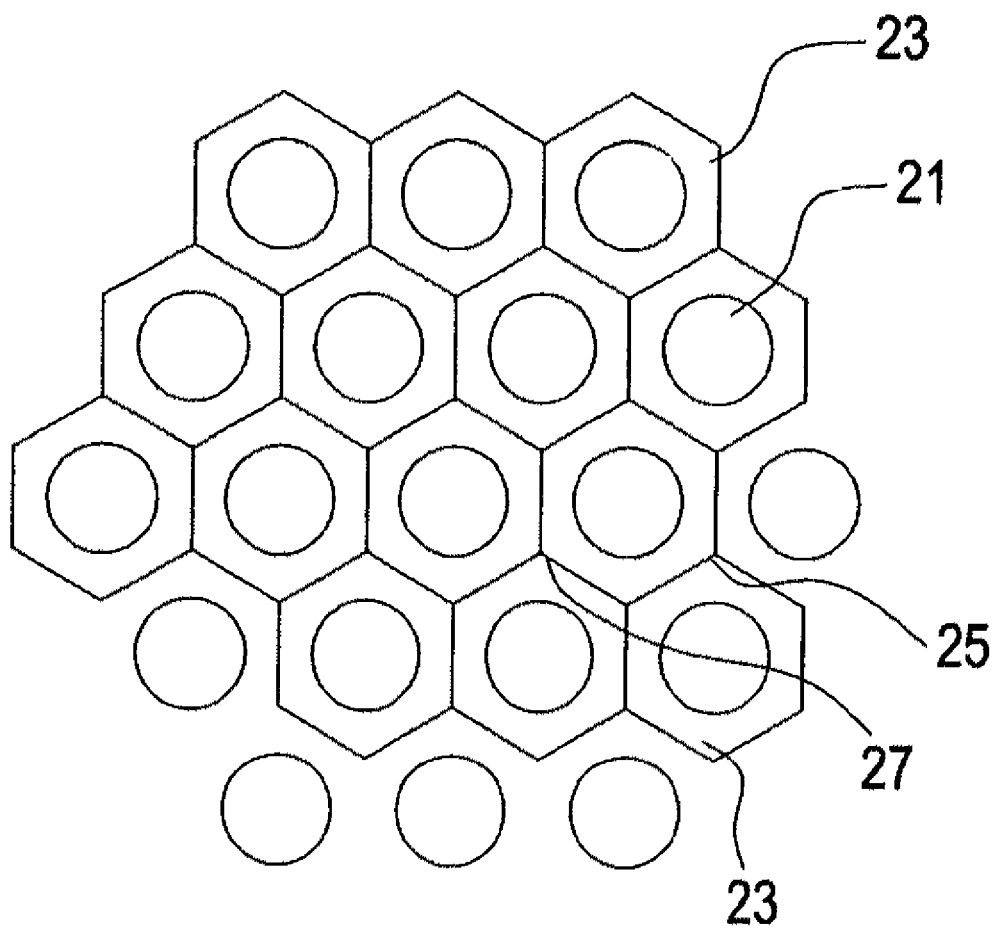
FIGS. 3a and 3b show an appliqué CAD drawing (3a) and resultant burr SEM photomicrograph (3b) for "hex" cutting design.
Figure 3B:
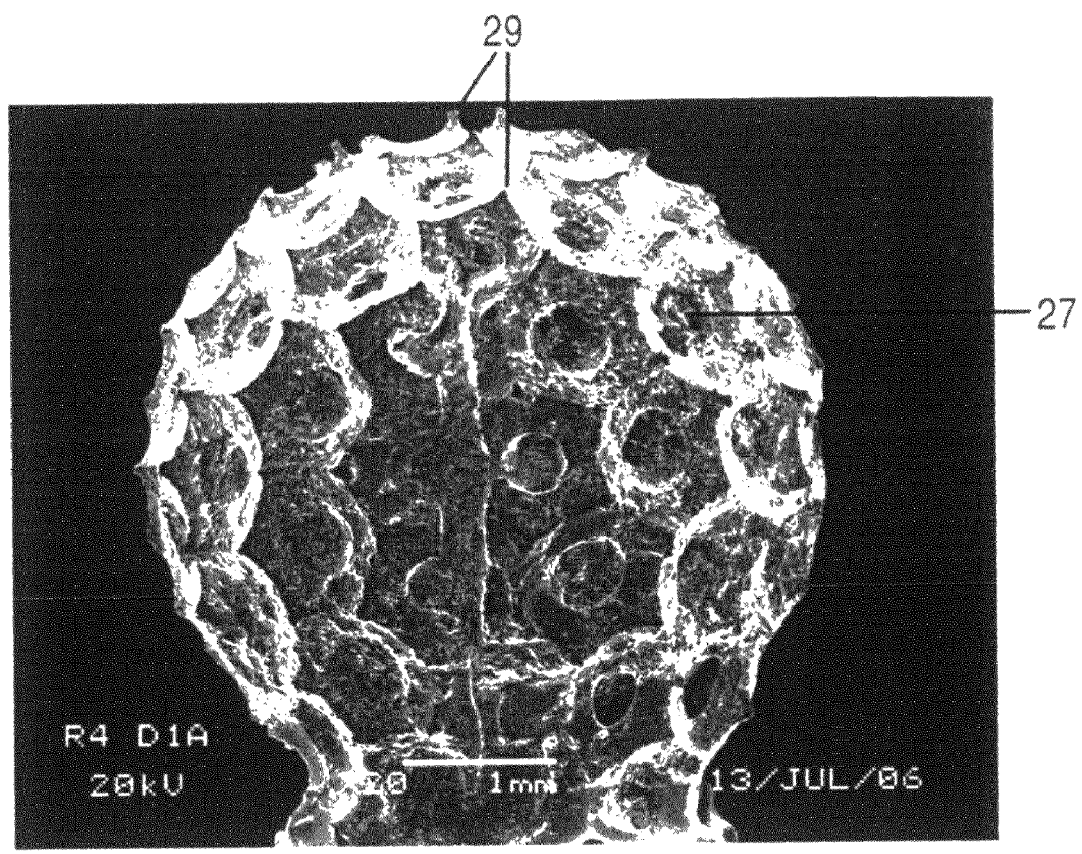

With reference to FIGS. 3a and 3b, a second example of a preferred cutting facet layout shear consists of a plurality of holes 21 surrounded by upturned generally hexagonal portions 23 which act as shear ridges. The corners of the hexagonal protrusions 23, for example, 25 and 27, come to a point distally of the holes 21. This is seen with reference to FIG. 3b with the points being designated by the reference numeral 29.

Figure 4A:
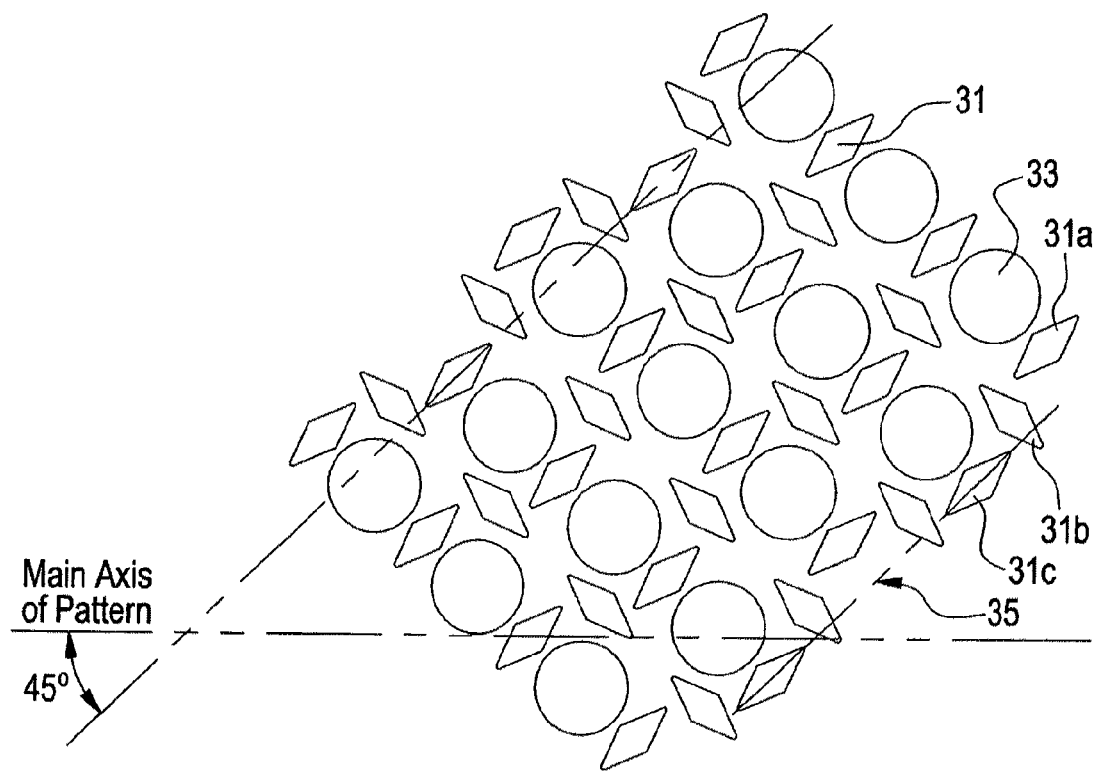
FIGS. 4a and 4b show an appliqué CAD drawing (4a) and resultant burr SEM photomicrograph (4b) for "diamond" cutting design.
Figure 4B:
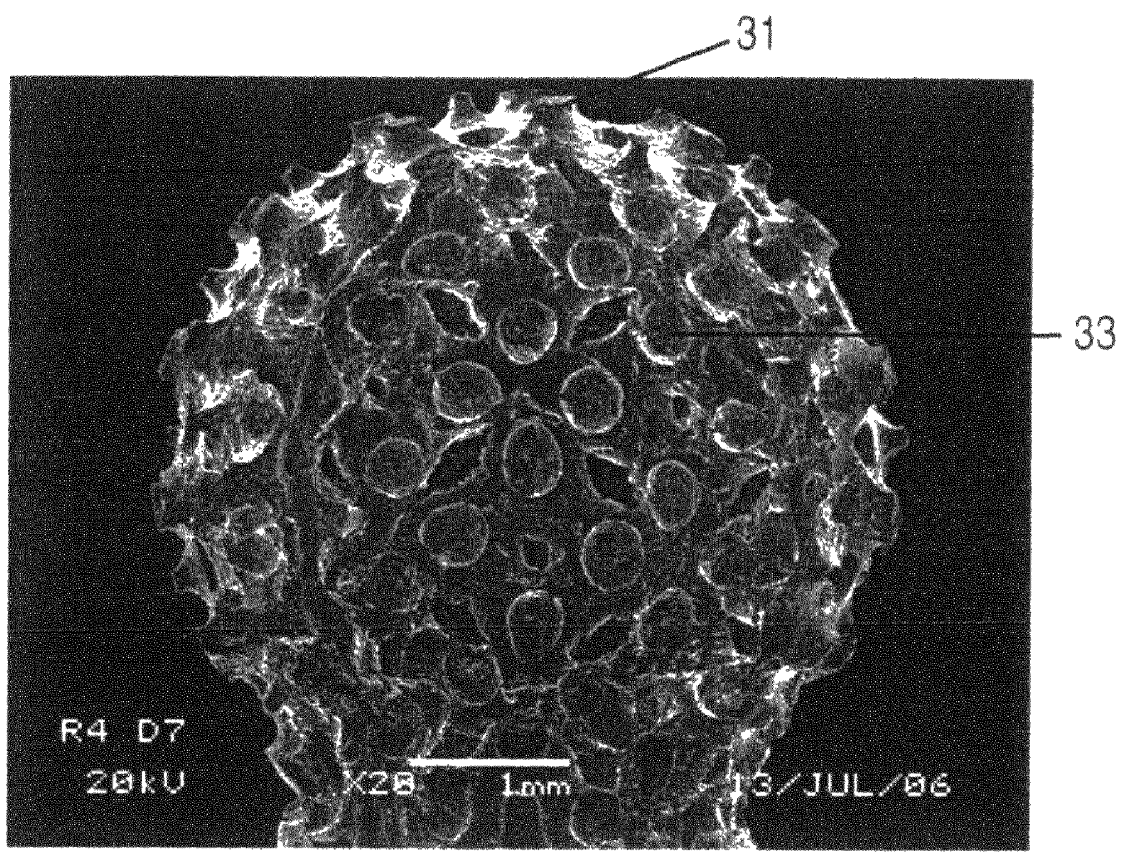

With reference to FIGS. 4a and 4b, a further preferred cutting facet layout is seen to include a plurality of diamond shaped protrusions 31 and a plurality of holes 33. As seen, adjacent protrusions 31 have axes of elongation 35. Adjacent protrusions 31 have their axes of elongation oriented perpendicularly with respect to one another. This is seen, for example, with reference to the protrusion 31a and the protrusions 31b and 31c adjacent thereto. The degree of protrusion of the protrusions 31 is seen with reference to FIG. 4b.

The protrusions or facets may also take on the following shapes: conical, pyramidal, truncated conical or truncated pyramidal. The truncated shapes define flat plateaus that may have any of the following shapes: triangular, round, diamond-shaped, square, rectangular, and irregular shapes.

A variety of manufacturing processes may be used to create the appliqué but, in the preferred embodiment, photochemical etching is used. The patterns shown in FIGS. 2-4 are photographically transferred to a photo resist film like, but not limited to, DuPont Laminar HG. This is done by placing a transparency containing the design on the film and exposing it to UV light. A chemical change occurs in the film in areas not covered by the pattern. The film is pressed onto the appliqué sheet material and exposed to an alkaline solution.

This solution dissolves the film from areas not covered by the cutting facet pattern. Now the appliqué sheet material, with pattern attached, is exposed to a strong etchant, like ferric chloride, in the case of a metallic appliqué. Unwanted material is etched away leaving protrusions or cutting facets where the appliqué sheet was covered with the pattern.

Facet depth is controlled by the starting thickness of the appliqué material photochemical etching parameters such as time in solution. Holes are created in the same manner by etching through the material thickness. Photochemical etching parameters are adjusted to leave a web pattern and holes between protrusions as seen in FIGS. 2-4.

The web pattern connects all cutting facets so each is supported and prevented from being dislodged later during use. Holes are used for communication of the BRAZOL® material from the outer surface of the appliqué to the inner surface thereof which interfaces with the tool blank for bonding. Both the web pattern and holes enable forming of the appliqué on the tool blank surface.

Figure 1A:
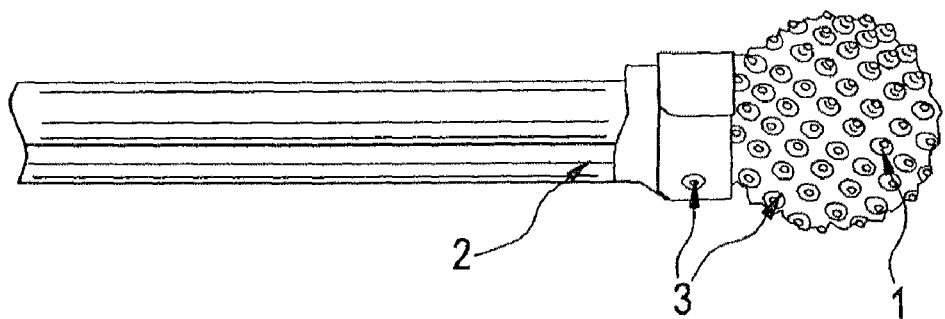
FIGS. 1a, 1b and 1c consist of enlarged photographs of a medical burr and abraders with appliqués metallurgically bonded and coated by the BRAZOL® coating and process.
Figure 1B:
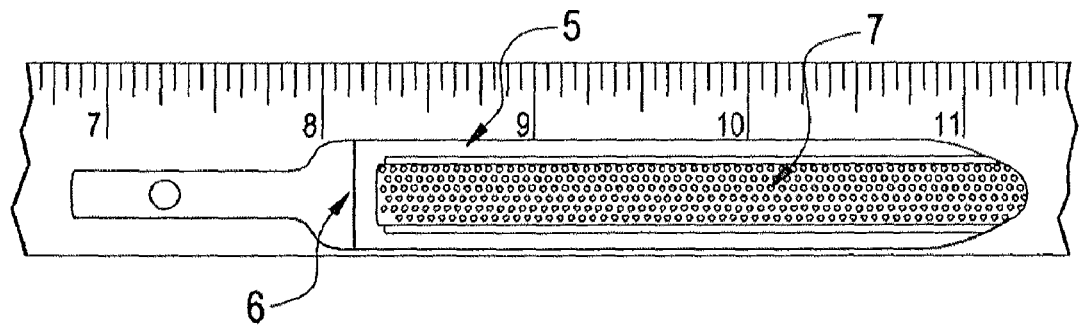
Figure 1C:
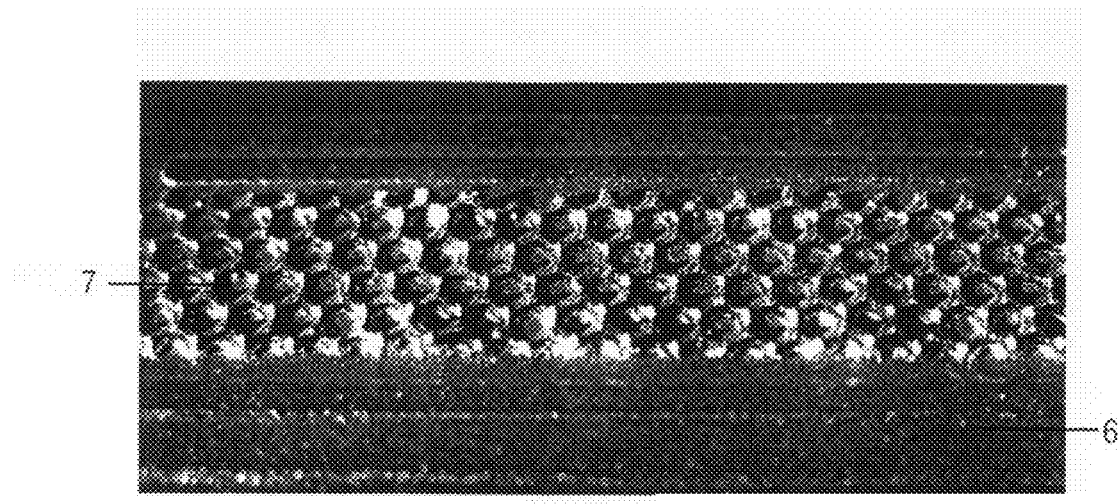

With reference to FIGS. 1a, 1b and 1c, attachment of an appliqué to a tool blank is shown. Thus, FIG. 1a shows a burr 1 made of a tool blank 2 on which an appliqué 3 such as that which is shown in FIGS. 2a and 2b has been attached and coated using the BRAZOL® material and process. FIG. 1b shows an abrader 5 having a surface 6 on which an appliqué 7 has been attached and coated using the BRAZOL® material and process. FIG. 1c shows an enlarged view of the abrader 5 of FIG. 1b showing details of the pattern of protrusions on the appliqué 7.

Figure 5:
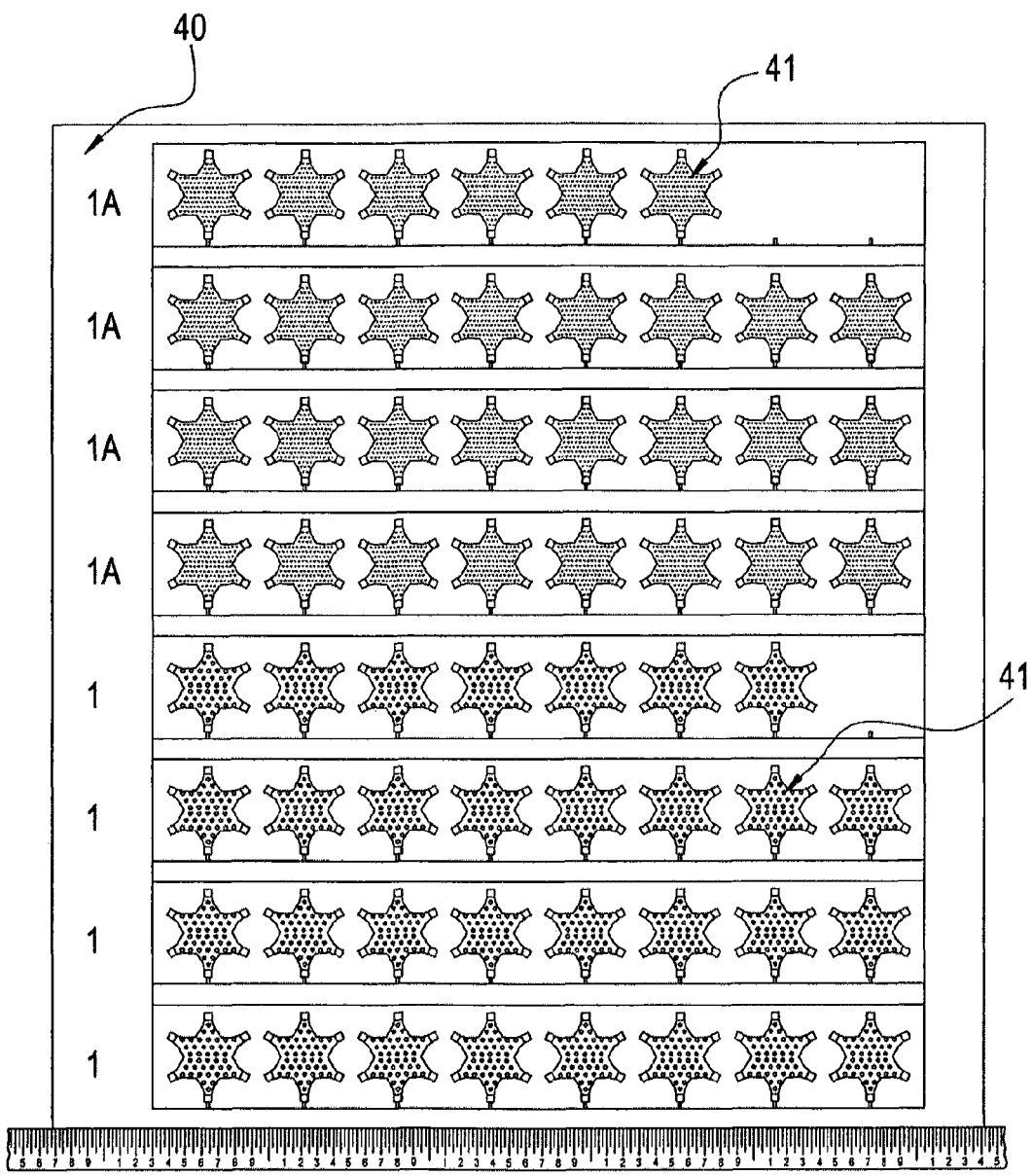
FIG. 5 shows a photograph of multiple appliqués simultaneously made from a single sheet of material.

In the preferred embodiments, the web pattern is typically 0.002-0.003" thick while the protrusions are typically 0.010-0.015" deep. Holes, when used, are typically 0.005 to 0.050" in diameter. As seen in FIGS. 2a-4b, facet size is typically 0.001-0.020" diameter or major/minor axis, but can be reduced to a point as shown in FIGS. 2a-b "Hex" design. Facet spacing can vary from 0.005 to 0.070" and facet depth can be 0.001 to 0.032". Of course, for manufacturing economy, a multitude of appliqués 41 are made from a single sheet of material 40 as seen in FIG. 5. Good repeatability of design and sharpness of detail result from this process as seen in FIG. 5 where individual appliqués 41 are depicted.

This engineering approach to designing the cutting pattern offers the user a custom cutting action for each specific application. For example, the hexagonal pattern seen in FIGS. 3a and *b* has the advantage of not only having cutting facets but also small shear ridges between facets. This type of cutting pattern can first create "furrows" with sharp facet points and then remove material between by shearing with ridges. This cutting action is superior to the gross tearing pattern presented by diamond burrs in applications like bone surgery.

Other manufacturing processes that may be used to create the appliqué include electro-discharge machining (EDM), laser etching and drilling, water jet cutting and drilling, conventional milling and drilling, powder metallurgy, casting, and electro-chemical milling.

After the appliqués 41 are formed as part of the sheet 40 (FIG. 5), they are then separated from the sheet 40 and formed around the burr blank or tool surface shown in FIGS. 1*a*-4*b*. The appliqués are attached to the blanks in preparation for the BRAZOL® process by welding with a variety of techniques. In the preferred embodiment, capacitor discharge resistance welding is used. BRAZOL® bonding and coating or Cobalt-Phosphorous (Co—P) bonding and coating are used to metallurgically bond and coat the appliqué to the burr or tool blank as described in the referenced patents. The BRAZOL® or Co—P material may be applied in the form of a powder over the appliqué or it may be preplaced between the appliqué and burr blank surface. The holes in the appliqués allow the bonding material to flow therethrough during bonding to enhance the connection. Other forms of the BRAZOL® or Co—P material may be used such as foil, sintered preform, adhesive bonded preform, or by plating. The BRAZOL® or Co—P bonding and coating process is done at high temperature in a vacuum furnace wherein the BRAZOL® or Co—P material is melted and metallurgical bonding is accomplished. The BRAZOL® or Co—P bonding and coating process is done at temperatures from 1650 to 2075° F. in a vacuum furnace in which the BRAZOL® or Co—P material is melted and metallurgical bonding is accomplished. The temperature depends on the bonding/coating material composition selected. In a preferred embodiment for the practice of the BRAZOL® process, the temperature cycle used is:

Heat to 800 to 1000° F. for about 30 minutes;
Then heat to 1550 to 1575° F. for about 30 minutes;
Then heat to 1850 to 1900° F. for about 15 minutes.

In a preferred embodiment for practice of the Co—P process, the temperature cycle used is:

Heat to 800 to 1000° F. for about 30 minutes;
Then heat to 1550 to 1600° F. for about 30 minutes;
Then heat to 1985 to 1995° F. for about 25 minutes.

The vacuum level for both processes is $10^{-3}$ torr or better. Alternatively, the cycles may be run in a protective gas, either inert or reactive, such as argon, nitrogen, hydrogen or mixtures of same. In a preferred embodiment for both cycles, pure hydrogen with a dew point of −60° F. or better is employed.

This metallurgical bonding process ensures that the appliqué will not be dislodged during use. The appliqué material and BRAZOL® or Co—P coating combination will deform with use rather than fracture and dislodge. The BRAZOL® or Co—P coating provides wear resistance and lubricity to the cutting surfaces so burr debris is eliminated and frictional heating is minimized. Lubricious protrusions and interspersed recesses aid in cutting debris rejection and removal. Other surface treatments may also be used on cutting facets to further improve performance. These include nitriding, carburizing, combinations of nitriding and carburizing, other diffusion treatments involving elemental additions to the surface such as chromium, and physical vapor deposition processes.

The burr with bonded and coated appliqué is operated in a rotary powered hand piece (not shown) in a preferred embodiment of this invention. As the rotating burr encounters the subject surface, the cutting facets remove and dislodge subject material. This material or debris exits the burr via spaces between facets. The burr can be used with or without lubrication. Since the pattern, shape and spacing of the cutting facets are non directional, no kickback occurs when the burr cuts, even when operated at low speeds. Generally, larger, deeper and more widely spaced protrusions produce a more aggressive cutting surface. Smaller, shallower, and closely spaced protrusions produce a less aggressive cutting surface for very fine work.

In a preferred embodiment of this invention, a medical burr is produced for removing bone and other tissue from a patient during surgery. Surgeries may involve preparing a bone surface to receive an implant or simply to remove unwanted bone or other tissue. Designs as shown in FIGS. 1*a*-5 are used, but other designs have been produced and reduced to practice in accordance with the principles of the present invention as explained above.

In another preferred embodiment of this invention, an appliqué surface is bonded and coated to a medical abrader that may be reciprocated, oscillated or hand manipulated. An example of a medical abrader used to remove bone tissue by being reciprocated on the bone surface is shown in FIGS. 1*b* and 1*c*. The appliqué has been metallurgically bonded and coated by the BRAZOL® process in FIGS. 1*b*-1*c*.

The appliqué material may be a metal such as a precipitation hardening stainless steel, or another stainless steel with good impact and strength properties. Other alloys include biocompatible materials such as titanium and cobalt base alloys. Ceramic, carbide, cermet, intermetallic compounds, and nanotechnology materials are other appliqué possibilities. Also, biodegradable materials such as plastics that can be surface or bulk hardened, may be used.

Similarly, the burr base material under the appliqué may be the same as the appliqué material. However, the two materials may be different. For example, the appliqué material may be selected on the basis of good impact and wear resistance, hardness, and ease of braze-ability and coat-ability. The underlying burr base material and shaft may be selected for high strength and resistance to bending as well as for enhanced bonding with the appliqué. Also, the burr and shaft may be different materials that are joined by welding and/or brazing. The burr base or tool base may be fabricated by many techniques such as conventional machining, casting, metal injection molding, electro-upsetting, and electro-discharge machining.

Materials for the tool blank may include stainless steel, low alloy steel, nickel base alloy, cobalt base alloy, titanium base alloy, powder metallurgy alloy, and a nanotechnology material.

In a preferred embodiment of this invention for a composite material medical burr, a 17-7 PH stainless steel (SS) appliqué was BRAZOL® bonded and coated to a 17-4 PH SS spherical ball and shank (FIG. 1*a*) referred to as a burr blank. The appliqué was made by photochemically etching annealed 17-7 PH SS sheet and the burr blank by machining from 17-4 PH SS annealed bar stock. The assembly was then precipitation hardened by vacuum furnace heat treatment to maximize mechanical properties of both the appliqué and the burr blank.

In a preferred embodiment of this invention for the medical abrader tool (FIGS. 1*b* and 1*c*), a 17-7 PH stainless steel (SS) appliqué was BRAZOL® bonded and coated to a Type 420 SS abrader blank. The appliqué was made by photochemically etching annealed 17-7 PH SS sheet and the abrader blank by stamping and machining from 420 SS annealed sheet. The assembly was then vacuum furnace heat treated to maximize mechanical properties of both the appliqué and the abrader blank.

These manufacturing techniques, cutting surface designs, surface modifications, and coatings are all applicable to flat and irregularly curved tools as well as spherical and hemispherical burrs and tools. Other embodiments of this invention include industrial applications where burr and abrader tools are used. Examples include removal of metals, plastics, fiber composites, wood products, ceramics, oxides and other minerals. These tools may also be used in drilling applications such as in the electronics and mining industries.

For example, this type of device may be used for printed circuit board drilling and cutting. Other composites may also be fabricated with this invention. Gem stone cutting and shaping/polishing are applications. Metals that have been hardened for applications like plastic, and metal injection molding dies can be trimmed and modified with this tool technology. Difficult to machine materials, like nickel and cobalt base superalloys, are applications for this invention.

As such, an invention has been disclosed in terms of preferred embodiments thereof which fulfill each and every one of the objects of the invention as set forth hereinabove, and provide an advanced burr, appliqué for a burr and method of fabricating of great novelty and utility.

Of course, various changes, modifications and alterations in the teachings of the present invention may be contemplated by those skilled in the art without departing from the intended spirit and scope thereof.

As such, it is intended that the present invention only be limited by the terms of the appended claims.

The invention claimed is:

1. An abrading device, comprising:
   a) a tool blank having a proximal shank and a base comprising a distal surface;
   b) an appliqué comprising a sheet of material, said sheet of material comprising a plurality of cutting facets integrally formed as parts of the sheet of material and a plurality of holes extending completely through said sheet of material, wherein said plurality of cutting facets and said plurality of holes form an abrading surface;
   c) said appliqué being fastened to said distal surface of said tool blank with a brazing alloy that metallurgically bonds over said appliqué to said distal surface;
   d) whereby said abrading surface is capable of engaging with a surface of an object to be abraded and capable of moving with respect to said object surface to abrade said object surface;
   e) said abrading surface being integrated on said appliqué to substantially eliminate creation of debris from said sheet of material while said abrading surface is abrading said object surface.

2. The device of claim 1, wherein said proximal shank is attachable to a rotary driver.

3. The device of claim 1, wherein said proximal shank is attachable to a reciprocating driver.

4. The device of claim 3, wherein said driver is an oscillating driver.

5. The device of claim 1, wherein said brazing alloy provides a wear resistant and lubricious surface.

6. The device of claim 1, wherein said brazing alloy is a nickel-base alloy.

7. The device of claim 1, wherein said brazing alloy is a cobalt-phosphorous base alloy.

8. The device of claim 1, wherein said appliqué substantially completely surrounds said distal surface.

9. The device of claim 1, wherein said brazing alloy fastens said appliqué to said distal surface by means including flowing through said plurality of holes, and forming a new surface alloy on said appliqué and said tool blank.

10. The device of claim 9, wherein said surface alloy is selected to provide a wear resistant and lubricious surface.

11. The device of claim 1, wherein said base comprises a sphere.

12. The device of claim 11, wherein said appliqué shape is adapted to conform to said distal surface for ease of forming to said distal surface and is shaped to include 2 to 8 points.

13. The device of claim 1, wherein said base comprises a hemisphere.

14. The device of claim 1, wherein said base is flat.

15. The device of claim 14, wherein said appliqué is flat.

16. The device of claim 1, wherein said plurality of cutting facets are interconnected.

17. The device of claim 16, wherein each of said plurality of facets has a diameter of 0.001 to 0.02 inches, a depth of 0.001 to 0.032 inches, and a spacing between adjacent facets of the plurality of facets of 0.005 to 0.070 inches.

18. The device of claim 16, wherein said plurality of facets have a shape chosen from the group consisting of conical facets, pyramidal facets, truncated conical facets and truncated pyramidal facets.

19. The device of claim 18, wherein said truncated conical facets and truncated pyramidal facets have flat plateaus with peripheral shapes chosen from the group consisting of triangular, round, diamond-shaped, square, rectangular and irregularly-shaped.

20. The device of claim 1, wherein said plurality of holes are each 0.005 to 0.050 inches in diameter.

21. The device of claim 1, wherein said tool blank is made from a material chosen from the group consisting of stainless steel, low alloy steel, nickel base alloy, cobalt base alloy, titanium base alloy, alloy formed during conducting of a powder metallurgy process, and composite material.

22. The device of claim 21, wherein said proximal shank is attachable to a driver chosen from the group consisting of rotary, reciprocating, and oscillating.

23. An abrading device, comprising:
   a) a tool blank having a proximal shank attachable to a driver chosen from the group consisting of rotary, reciprocating, and oscillating, and a base comprising a distal surface;
   b) an appliqué comprising a sheet of material, said sheet of material comprising a plurality of cutting facets integrally formed as parts of the sheet of material and a plurality of holes extending completely through said sheet of material, wherein said plurality of cutting facets and said plurality of holes form an abrading surface;
   c) said appliqué being fastened over said distal surface of said tool blank by a brazing alloy chosen from the group consisting of a nickel base alloy and a cobalt-phosphorous base alloy;
   d) whereby said abrading surface is capable of engaging with a surface of an object to be abraded and capable of moving with respect to said object surface to abrade said object surface;
   e) said appliqué substantially completely covering said distal surface;
   f) said abrading surface being integrated on said appliqué to substantially eliminate creation of debris from said sheet of material while said abrading surface is abrading said object surface.

24. The device of claim 23, wherein said brazing alloy fastens said appliqué to said distal surface by means including flowing through said plurality of holes.

25. The device of claim 23, wherein said plurality of facets each have a diameter of 0.001 to 0.020 inches, a depth of 0.001 to 0.032 inches, and a spacing between adjacent facets of 0.005 to 0.070 inches.

26. The device of claim 25, wherein said facets have a shape chosen from the group consisting of conical facets, pyramidal facets, truncated conical facets, and truncated pyramidal facets.

27. The device of claim 26, wherein said truncated conical facets and truncated pyramidal facets have flat plateaus with peripheral shapes chosen from the group consisting of triangular, round, diamond-shaped, square, rectangular and irregularly-shaped.

28. The device of claim 23, wherein said tool blank is made from a material chosen from the group consisting of stainless steel, low alloy steel, nickel base alloy, cobalt base alloy, titanium base alloy, alloy formed during conducting of a powder metallurgy process, and composite material.

\* \* \* \* \*